United States Patent
Zinkel

(10) Patent No.: US 7,210,485 B2
(45) Date of Patent: May 1, 2007

(54) METHOD FOR SPINAL SURGERY

(75) Inventor: John M. Zinkel, St. Clair Shores, MI (US)

(73) Assignee: C & J Holdings, LLC, St. Clair Shores, MI (US)

( * ) Notice: Subject to any disclaimer, the term of this patent is extended or adjusted under 35 U.S.C. 154(b) by 106 days.

(21) Appl. No.: 10/848,265

(22) Filed: May 18, 2004

(65) Prior Publication Data

US 2004/0215199 A1 Oct. 28, 2004

Related U.S. Application Data

(62) Division of application No. 10/210,147, filed on Aug. 1, 2002.

(51) Int. Cl.
*A61B 19/00* (2006.01)
*A61B 1/32* (2006.01)

(52) U.S. Cl. .................. 128/898; 600/210; 600/219

(58) Field of Classification Search ............. 600/235, 600/201, 210, 219, 222; 606/86, 90
See application file for complete search history.

(56) References Cited

U.S. PATENT DOCUMENTS

| | | | |
|---|---|---|---|
| 3,789,852 A | 2/1974 | Kim et al. ................. | 128/347 |
| 4,130,113 A | 12/1978 | Graham ...................... | 128/20 |
| 4,747,394 A | 5/1988 | Watanabe .................. | 128/20 |
| 4,899,729 A | 2/1990 | Gill et al. ................... | 128/3 |
| 5,052,373 A | 10/1991 | Michelson .................. | 128/20 |
| 5,125,396 A * | 6/1992 | Ray ............................ | 600/208 |
| 5,363,841 A | 11/1994 | Coker ......................... | 128/20 |
| 5,429,121 A | 7/1995 | Gadelius ..................... | 600/217 |
| D361,381 S | 8/1995 | Koros et al. ................ | D24/135 |
| 5,512,038 A | 4/1996 | O'Neal et al. .............. | 600/210 |
| D369,860 S | 5/1996 | Koros et al. ................ | D24/135 |
| D380,548 S | 7/1997 | Koros et al. ................ | D24/135 |
| 5,741,261 A * | 4/1998 | Moskovitz et al. ........... | 606/79 |
| 5,792,044 A | 8/1998 | Foley et al. ................. | 600/114 |
| 5,902,233 A | 5/1999 | Farley et al. ............... | 600/213 |
| 5,931,777 A * | 8/1999 | Sava .......................... | 600/213 |
| 5,967,970 A * | 10/1999 | Cowan et al. ............... | 600/207 |
| 6,196,969 B1 * | 3/2001 | Bester et al. ................ | 600/224 |
| 6,206,826 B1 | 3/2001 | Mathews et al. ............ | 600/210 |
| 6,224,597 B1 | 5/2001 | Coker ......................... | 606/61 |
| 6,241,729 B1 | 6/2001 | Estes et al. ................. | 606/61 |
| 6,277,094 B1 * | 8/2001 | Schendel .................... | 604/104 |
| 6,296,609 B1 | 10/2001 | Brau .......................... | 600/210 |
| 6,302,842 B1 * | 10/2001 | Auerbach et al. ........... | 600/220 |
| 6,309,349 B1 * | 10/2001 | Bertolero et al. ........... | 600/213 |

(Continued)

OTHER PUBLICATIONS

Abram, Leon, Dilation Discectomy, Jul. 2001, Spinal Concepts, Document 1999-0006-MKC Re. A Per DCR 1327.*

*Primary Examiner*—Cary E. O'Connor
(74) *Attorney, Agent, or Firm*—Gifford, Krass, Sprinkle, Anderson & Citkowski, P.C.

(57) ABSTRACT

Spinal surgery is carried out under direct visualization through a relatively small opening formed in a patient's skin. Intervening tissue between the opening and the surgical site is displaced so as to form a keyhole channel therethrough. The channel is characterized in that it increases in width as it progresses from the opening to the surgical field. The use of the keyhole channel maximizes the surgeon's access to the surgical field while minimizing tissue trauma. Also disclosed are surgical retractors used to provide the channel.

14 Claims, 3 Drawing Sheets

U.S. PATENT DOCUMENTS

| | | | |
|---|---|---|---|
| 6,666,891 B2 * | 12/2003 | Boehm et al. | 623/17.16 |
| 6,684,886 B1 | 2/2004 | Alleyne | 128/898 |
| 6,869,398 B2 * | 3/2005 | Obenchain et al. | 600/224 |
| 2002/0072752 A1 * | 6/2002 | Zucherman et al. | 606/99 |
| 2003/0083689 A1 * | 5/2003 | Simonson | 606/191 |

* cited by examiner

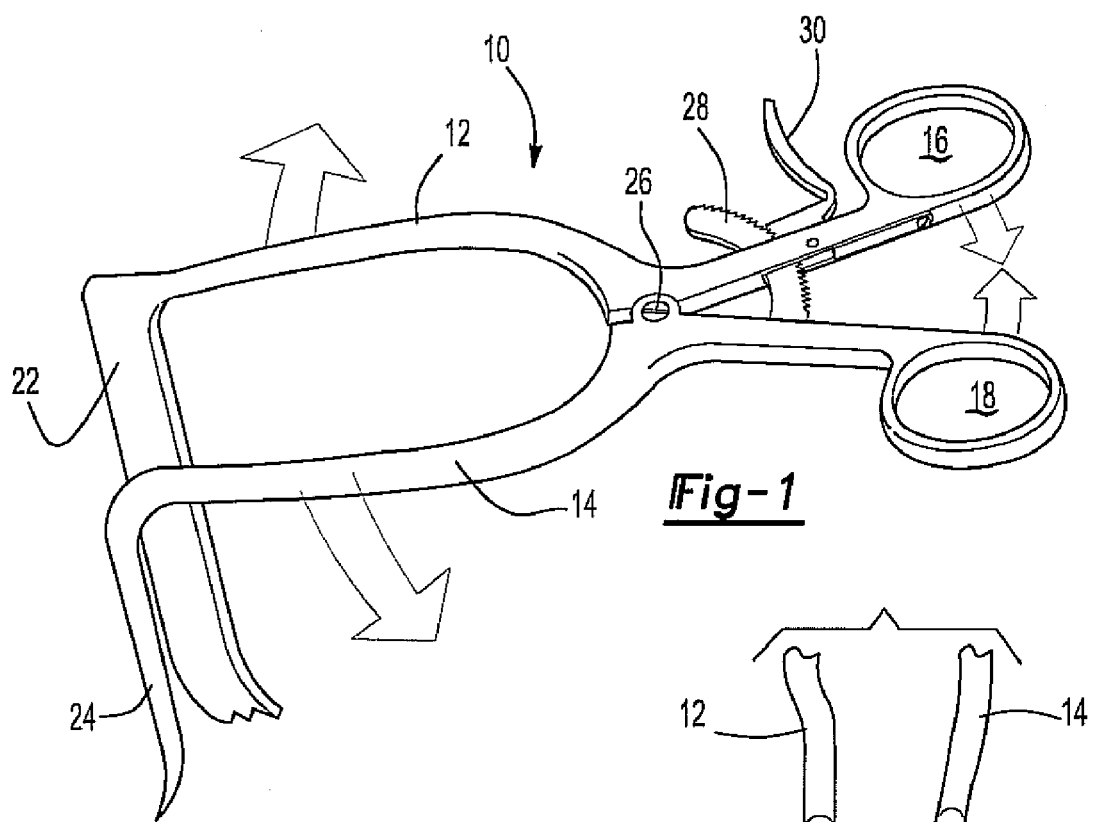
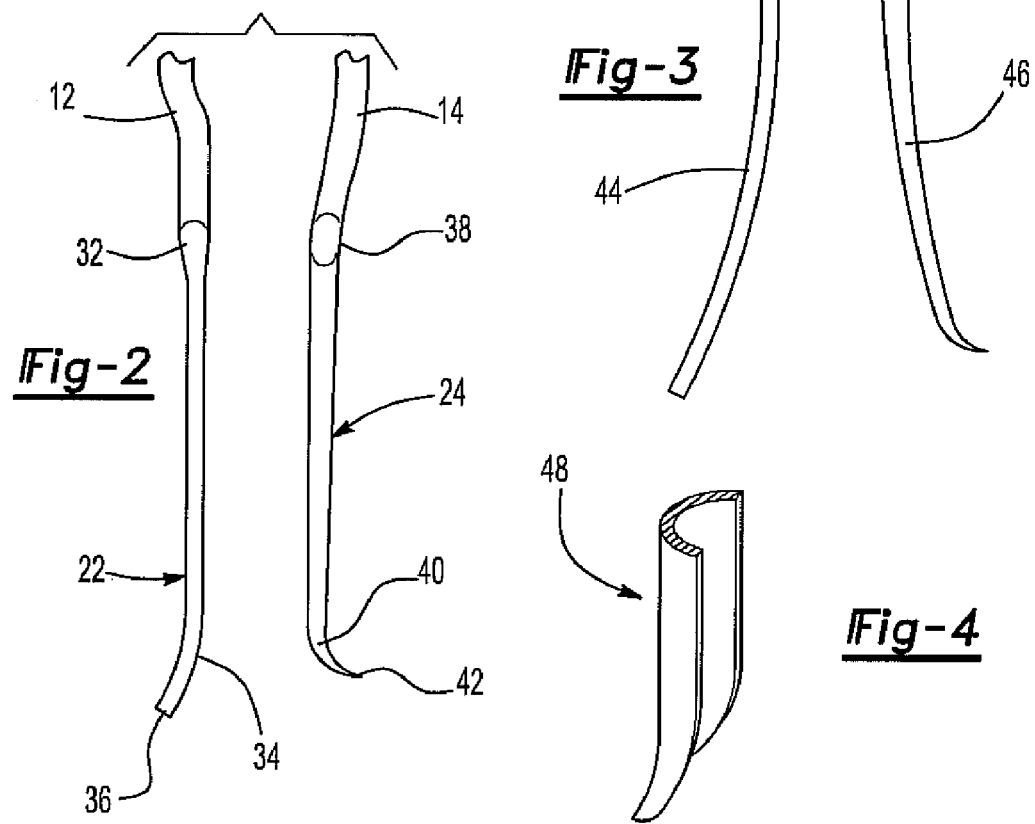

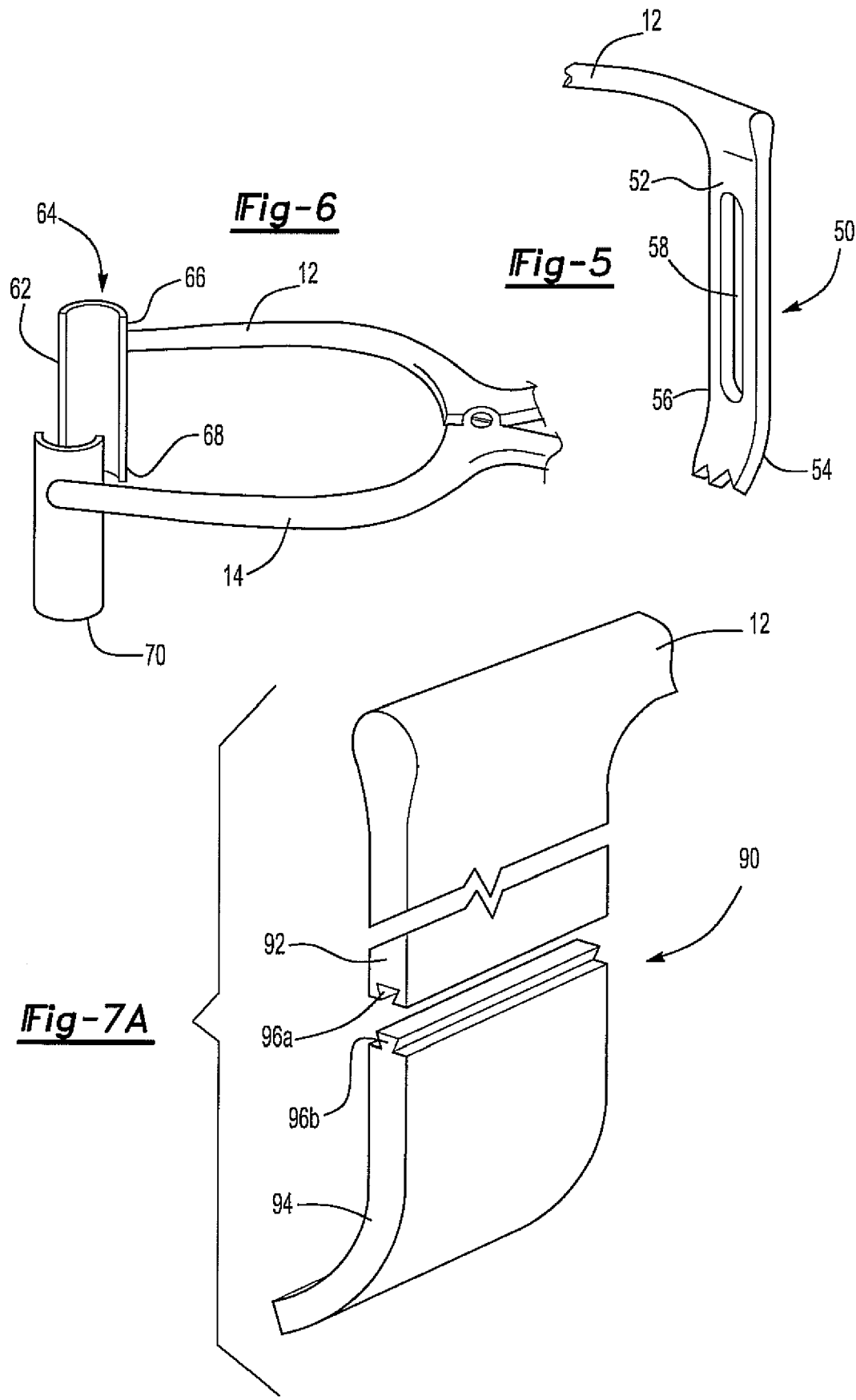

METHOD FOR SPINAL SURGERY

RELATED APPLICATION

This application is a divisional of U.S. patent application Ser. No. 10/210,147 filed Aug. 1, 2002.

FIELD OF THE INVENTION

This invention relates generally to surgical methods and instruments. More specifically, the invention relates to methods and instruments for spinal surgery. Most specifically, the invention relates to a surgical retractor and methods for its use whereby spinal surgery may be carried out at an open surgical field, under direct visualization, with minimal trauma to intervening tissue.

BACKGROUND OF THE INVENTION

Spinal surgeries such as laminectomies, discectomies, fusions and the like are needed by a great many patients. The fact that the spine is a complex construction of bone, cartilage and nerves surrounded by relatively strong muscles makes spinal surgery difficult to perform and requires a high degree of skill on the part of the surgeon if successful results are to be obtained. Initially, all such spinal surgeries were carried out by what is referred to as "open" procedures wherein the spinal structures being operated upon were exposed via a relatively large skin incision that narrows down in conical fashion to the deep, bony operative target, cutting and destroying intervening soft tissue structures. Formation of the large open incision involved severing and separating a large number of tendons, ligaments, and muscle fibers, and this tissue trauma has been found to cause the patient pain, prolonged hospital stays, prolonged recovery and permanent low back weakness. In addition, many patients were dissatisfied with the scarring resultant from large-scale open procedures. Open procedures and apparatus for their implementation are disclosed in the prior art; see U.S. Pat. Nos. 5,052,373 and 5,363,841.

In an attempt to minimize problems associated with large-scale open spinal surgeries, the prior art developed a number of minimally invasive techniques. These techniques are often referred to as "percutaneous" and are typically implemented through the use of endoscopic devices. Such percutaneous techniques involve minimal ("puncture") incisions and are less traumatic to the patient. However, endoscopic visualization techniques are limiting insofar as the image provided thereby is a two-dimensional image with compromised resolution, for example an image displayed on a video monitor or visualized through a fiber optic viewing device. Furthermore, many such techniques require that the operation be carried out in a surgical field that is filled with a liquid such as a saline solution, or with a gas such as carbon dioxide. Also, if the endoscope and the surgical instruments are passed, by a cylindrical retractor, through the same access port, depth perception and the normal, bimanual use of instruments is greatly hindered. As a consequence, prior art percutaneous techniques are of limited utility. Such techniques are shown in U.S. Pat. Nos. 5,792,044 and 6,206,826.

As a result of the shortcomings of prior art open and percutaneous surgical techniques, spinal surgeons have sought alternative methods whereby spinal surgery may be carried out with minimal tissue invasion, but with maximized visualization of, and access to, the surgical field. Toward that end, direct visualization techniques have been developed wherein a relatively minor incision is formed in the patient's skin, and underlying tissues are displaced through the use of a dilator device, which may comprise a series of dilator mandrels having progressively greater diameters, or through the use of an expansible cannula. The dilator device displaces muscle tissue with minimal tearing or cutting, in a manner analogous to that of a blunt needle being forced through a woven cloth. Once an appropriately sized channel is dilated through the tissue, a working cannula is disposed in the dilated channel, and surgery takes place through the cannula. While this technique does allow for direct visualization and an open surgical field, the dilator devices and cannulae of the prior art provide a cylindrical working passageway through the tissue. This passage has a fairly high aspect ratio insofar as the diameter of the passage is relatively small compared to the passage length. Consequently, the surgeon has a difficult time manipulating instruments through the long narrow channel; furthermore, the geometry of the channel impedes binocular vision of the surgical field. As a consequence, it is often necessary to reposition the cannula during surgery to provide better visualization and/or access. Such repositioning is time consuming, and can tear muscle tissue or cause other undesired surgical trauma. Furthermore, the cylindrical cannula still limits the surgeon's vision and restricts the use of instruments, since access is still provided through a cylindrical channel.

In partial response to the shortcomings of the aforementioned minimally invasive, cannula based techniques, the prior art has developed a transparent walled cannula device which, following tissue dilation, is disposed in the dilated passage. The transparent walls of the cannula enhance visualization of the surgical site. However, the passage defined through the tissue is still cylindrical, and problems of access remain. Such apparatus, and techniques for its use are disclosed in a publication entitled *Dilation Discectomy: A System For The Surgeon*, Abram, Leon J. M.D., paper published at the 2001 International Intradiscal Therapy Society (IITS) Meeting, and republished July 2001 by Spinal Concepts Inc. as document number 1999-0006-MKC Rev. A per DCR #1327.

In view of the foregoing, it will be appreciated that there is a need for methods and apparatus whereby a surgeon may carry out spinal surgery under direct visualization with minimal patient trauma. Such techniques should provide a surgeon with a good view of, and access to, the surgical site. Furthermore, it is desirable that such techniques and apparatus be simple and reliable. As will be explained in detail hereinbelow, the present invention provides surgical instruments and techniques which fulfill these requirements. These and other advantages of the invention will be apparent from the drawings, discussion and description which follow.

BRIEF DESCRIPTION OF THE INVENTION

There is disclosed herein a surgical retractor having a first arm and a second arm. A first end of each arm defines a handle portion thereof, and a second end of each arm has a retractor blade projecting therefrom. The arms are pivotally connected together at a connection point between their respective first and second ends. Each retractor blade includes a junction end at which it is permanently affixed to its respective arm and a free end. The arms and blades are configured and disposed so that when, using the retractor, the arms are pivoted about the connection point, the free ends of the blades are always at least as far apart as are the junction ends. In specific embodiments, the retractor is configured so that when the arms are pivoted about the connection point in the use of the retractor, the free ends of the blades are always farther apart than are the junction ends. In specific embodiments, the blades may include straight and/or curved portions, and in one particular group of embodiments, at least one of the blades is curved transverse to its length. In one particular embodiment, the width dimension of each of the blades is no greater than 20 millimeters.

Also disclosed is a method for performing spinal surgery. The method comprises forming an opening through the skin of a patient, said opening having a maximum dimension of no more than 20 millimeters, and being separated from a surgical field by intervening tissue. In a subsequent step, the intervening tissue between the opening and the surgical field is displaced so as to form a keyhole channel therethrough, said keyhole channel being characterized in that it increases in width as it progresses from the opening to the surgical field. In this manner, the area of the surgical field at its depth exposed by the channel is greater than the area of the opening through the patient's skin. According to the method of the present invention, a surgical procedure can be implemented under direct visualization.

In a specific embodiment, the keyhole channel is formed by providing a passage through the intervening tissue, as for example by the use of a dilator device, and then inserting the blades of a retractor into the passage and separating the blades so as to displace the intervening tissue and form the keyhole channel. The dilator may comprise a series of dilator mandrels, each having a different diameter, or it may comprise an expansible member. The blades of the retractor may be inserted into the passage either before or after the dilator is withdrawn therefrom. The retractor of the present invention is particularly well suited for use in this surgical procedure.

BRIEF DESCRIPTION OF THE DRAWINGS

FIG. 1 is a perspective view of a retractor structured in accord with the principles of the present invention;

FIG. 2 is a perspective view of the retractor of FIG. 1, taken from the front end thereof, and showing the configuration of the retractor's blades;

FIG. 3 is a front perspective view of the blades of another embodiment of retractor;

FIG. 4 is a cross-sectional view, in perspective, of yet another embodiment of retractor blade;

FIG. 5 is a side elevational view of another retractor blade of the present invention;

FIG. 6 is a front, perspective view of the blades of yet another embodiment of retractor of the present invention;

FIG. 7A is a perspective view of a retractor blade of the present invention, as used in combination with an extension member;

DETAILED DESCRIPTION OF THE INVENTION

Figure 7B:
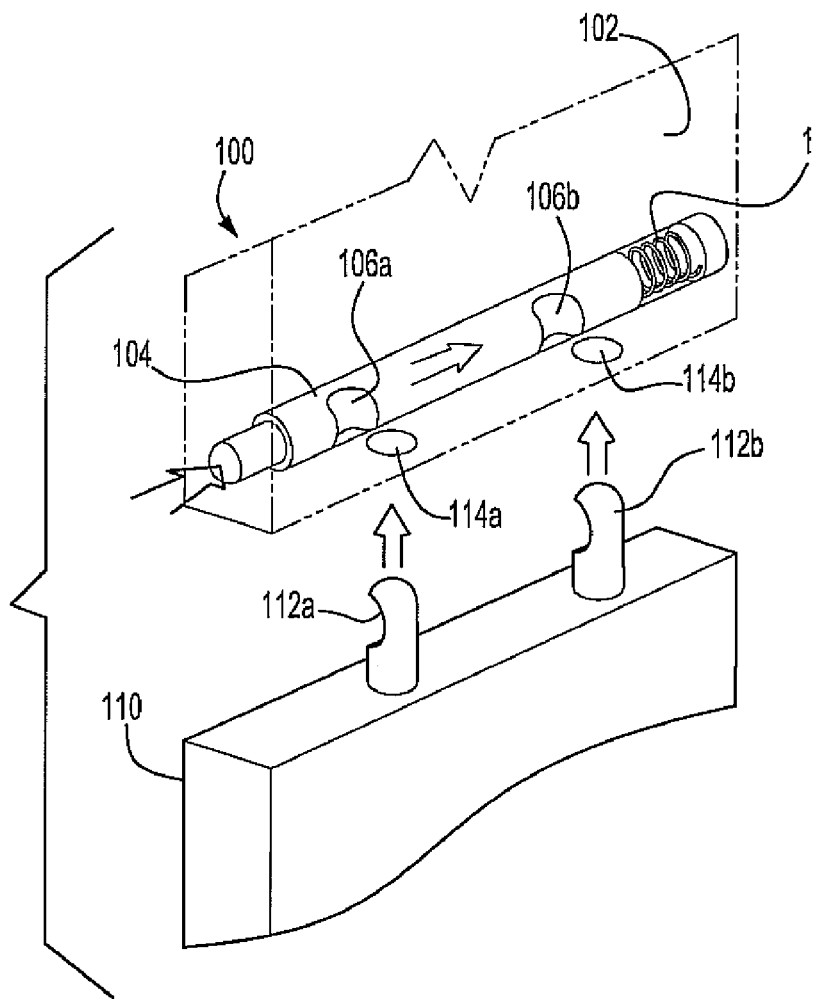
FIG. 7B is a perspective view showing a locking mechanism for retaining an extension member onto a retractor blade, in accord with the present invention.

The present invention provides a method and apparatus whereby surgery, and in particular, spinal surgery, may be carried out in an open surgical field with minimal patient trauma. The method and apparatus of the present invention employs a keyhole surgical opening which accords a surgeon a maximum operating field and necessitates only a minimal incision. The open procedure allows direct visualization of the surgical field, either with the naked eye or through the use of optical devices such as surgical microscopes and/or loupes the like, and thereby eliminates the need to employ devices such as endoscopes. The keyhole surgical opening permits a surgeon to utilize normal binocular vision and provides ready access for surgical tools.

In a particular aspect of the present invention, a specialized surgical retractor is utilized to provide the keyhole access opening. Referring now to FIG. 1, there is shown a perspective view of one embodiment of retractor 10 structured in accord with the principles of the present invention. The retractor 10 of FIG. 1 bears some general similarity to retractors of the prior art generally known as Williams retractors, Gelpi retractors, Velpi retractors, Caspar retractors, or Ducker retractors; however, and as will be explained hereinbelow, the retractor 10 of the present invention differs therefrom with regard to some significant details.

The retractor 10 of FIG. 1 includes a first arm 12 and a second arm 14. Each arm 12, 14 has a first end which terminates in a handle portion; and each handle portion as shown herein is configured as a loop 16, 18, although it is to be understood that the handle portion may be otherwise configured. For example, the handle portions may be configured as handgrips; they may be straight or curved, or otherwise shaped. Each arm 12, 14 also includes a retractor blade 22, 24 at a second end thereof. These blades, 22, 24 are shown in greater detail in FIG. 2, and will be discussed hereinbelow with reference thereto. The arms 12, 14 of the retractor 10 are pivotally connected together at a connection point 26 disposed between their respective first and second ends. As shown herein, each of the arms 12, 14 is bent so that when the two handle loops 16 and 18 are brought together, the blades 22, 24 are moved apart. In other embodiments, the arms may be otherwise configured so as to work in the opposite manner.

As is also shown in FIG. 1, the retractor 10 includes a locking mechanism for selectably immobilizing the arms 12, 14 relative to one another. This mechanism includes a toothed locking bar 28 which projects from the arm 14. This locking bar 28 passes through an opening (not shown) in the other arm 12, and is engageable by a locking lever 30 affixed to the other arm 12. This locking lever 30 is preferably spring biased and engages the toothed locking bar 28. In other embodiments, differently configured locking engagements may be employed as is known in the art, while in yet other embodiments the locking assembly may be further modified or eliminated.

Referring now to FIG. 2, there is shown a detailed depiction of the retractor blades 22, 24 of the FIG. 1 embodiment. As specifically shown therein, both retractor blades 22, 24 project from the second ends of their respective retractor arms 12, 14. In this embodiment, the blades 22, 24 project therefrom at approximate right angles; although, it is to be understood that in other embodiments, the blades may project at different angles. In accord with the present invention, the blades 22, 24 are permanently and rigidly attached to their respective arms 12, 14. This is important to ensure the integrity of and strength of the retractor device. Most preferably, the blades 22, 24 are formed integral with the arms 12, 14, as for example by forging or otherwise shaping the unitary piece of material. In other preferred embodiments, the blades 22, 24 are fixedly attached to their respective arms by welding, brazing or other such techniques. It has been found that such an integral structure provides very high strength for a given volume. Also, the integral nature of the structure facilitates sterilization.

As shown in FIG. 2, the first blade 22 is configured as a flattened, elongated member which is joined to its respective arm 12 at a junction end 32 thereof. While in this embodiment, the junction end terminates the blade 22, as will be discussed hereinbelow, in some instances, the blade may project some distance beyond the point at which the junction end 32 is joined to its respective arm 12. The blade 22 of FIG. 2 includes a relatively straight portion which commences at the junction end and runs for a portion of the length of the blade 22. The blade 22 also includes a curved portion 34 which commences at the free end 36 of the blade 22.

In the FIG. 2 illustration, the second blade 24 is shown as being a generally cylindrical spike. This second blade 24 is also integral with its respective arm 14, and includes a straight portion which commences at a junction end 38 of the blade 24, and a curved portion 40 which commences at a free end 42 of the blade 24. While the blades of the retractors of the present invention may be variously configured, it is generally preferred that at least one of the blades have a flattened (i.e. non-spiked) portion. The flatted portion, which may be of curved cross section as described below, is more effective in displacing tissue as compared to a spike configuration, which is best employed as a bone contacting member.

In accord with the present invention, the blades 22, 24 are configured and disposed so that when the retractor is in use and the arms 12, 14 are pivoted about the pivot point 26, the free ends 36, 42 of the blades 22, 24 are always at least as far apart from one another as are the junction ends 32, 28 of those blades. This configuration is in contrast to prior art retractors wherein the blades are configured so that the free ends are closer to one another than are the junction ends. The blades of such prior art retractors provide a generally V-shaped passage through tissue such that the bottommost portion of a surgical opening, proximate the surgical field being operated in, is smaller than the topmost portion of the access channel. Such prior art retractors limit the surgeon's access to the surgical field, while necessitating a relatively large opening through skin and tissue.

It is a notable feature of the retractor of the present invention that, in contrast to prior art retractors, the blades thereof are configured so that they are parallel to one another along their length and/or they diverge from one another as they progress from their junction ends to their free ends. As such, the retractor blades of the present invention provide a keyhole access channel for surgery.

While FIG. 1 and FIG. 2 depict one particular configuration of retractor and blades, it is to be understood that, in accord with the present invention, other configurations may be implemented. Referring now to FIG. 3, there is shown a view of a retractor generally similar to that of FIG. 2. The FIG. 3 retractor includes a first and second retractor arm 12, 14 also as discussed and described hereinabove. A first retractor blade 44, and a second retractor blade 46, project from their respective arms 12, 14 as described above. The retractor blades 44, 46 differ from the previously described blades insofar as they curve away from one another along their entire lengths. The first retractor blade 44 is of a generally flat cross section; it has an elongated shape as described above, and it curves along its entire length. The second retractor blade 46 is a spike shaped blade generally similar to the blade 24 described above, except that it also curves along its entire length. The blades 44, 46 function, as described above, to provide a keyhole access channel through tissue.

As shown in FIGS. 1–3, the retractors depicted include a first, relatively flat blade, such as blades 22 and 44, and a second, spike blade, such as blades 24 and 46. It is to be understood that the retractor may be otherwise configured. For example, a retractor may include two flat blades. As shown above, both blades are of approximately equal length; however, in some embodiments of the invention, the blades will differ in length. Also, the blades may be yet otherwise configured. For example, in some embodiments, either, or both, of the blades may include a relatively flat portion and a cylindrical, spiked portion. The flat portion may form the free end of the blade so that the blade is spoon-like, or the cylindrical spiked portion may form the free end.

In other instances it may be desirable to replace a flat blade with a blade which is curved in a direction transverse to its length. That is to say, a blade which is curved transverse to a longitudinal axis extending from its junction and to its free end. FIG. 4 depicts a cross-sectional perspective view of one such blade, with a cross section being taken in the direction of the curvature, and transverse to the longitudinal axis of the blade. The curved blade 48 of FIG. 4 has a relatively straight longitudinal axis with a terminal flare, as does the blade 22 of FIG. 2, or it may be longitudinally curved, as for example in the blade 44 of FIG. 3. The curvature of the blade is preferably disposed so that the convex side thereof contacts and displaces the patient's tissue when the retractor is in use. This type of curved blade can minimize pressure damage to tissue, particularly pressure damage which occurs at the edges of the blade. One or both of the retractor blades may have a curved cross section.

Referring now to FIG. 5, there is shown yet another variation of retractor blade structured in accord with the principles of the present invention. FIG. 5 depicts a relatively straight, flat, retractor blade 50 having a junction end 52, which is joined to a retractor arm 12 and a free end 56 with a relatively short curved portion 54 commencing thereat. As such, the blade 50 of FIG. 5 is generally similar to the blade 22 of FIG. 2. However, the blade 50 of FIG. 5 also includes an opening 58 running along a portion of its longitudinal axis. This opening 58 is configured to receive a portion of a corresponding retractor blade when the retractor is in its closed position. This configuration will minimize the profile of the closed retractor thereby enabling it to be inserted through a relatively small opening, while still permitting maximal tissue displacement when the retractor is open. As depicted in FIG. 5, the opening 58 passes entirely through the blade 50; however, in other embodiments, the opening may only pass partway through the blade and still secure the benefits of the invention.

Referring now to FIG. 6, there is shown yet another embodiment of retractor of the present invention. This embodiment includes a first and a second arm 12, 14 as previously described. It further includes a first and a second retractor blade 62 and 64. Each blade in this embodiment is configured as a curved blade, as generally described with reference to FIG. 4, and each blade has a straight longitudinal axis. In this embodiment, each blade 62, 64 projects above its respective retractor arm 12, 14 for a short distance past its junction end, for example junction end 66 of blade 64. In this regard, it is to be understood that the term "junction end" refers to that portion of the retractor blade which is joined to its respective arm even in those instances where a further projection of the blade extends beyond this point. In most instances, the blades will not include any such projection; however, relatively short projections, typically less than 25% of the length of the remainder of the blade, may be desirable to aid in positioning or to maintain the integrity of the opening.

The FIG. 6 embodiment is shown as having the longitudinal axes of each of the blades 62, 64 disposed generally parallel to one another. It is to be understood that other variations of this embodiment may be implemented in which the axes diverge from one another along their entire length, or flare apart from one another as they progress toward the free ends 68, 70 thereof.

In certain embodiments of the present invention, one or more of the retractor blades may be configured to receive and retain an extension portion thereupon. This extension portion can operate to change the length and/or profile of the blade without compromising the advantages achieved through the use of the present invention. Referring now to FIG. 7A, there is shown a perspective view of a portion of a retractor 90 which is so configured. As shown therein, a retractor blade 92 is permanently affixed to its respective retractor arm 12 as described hereinabove. However, this retractor blade 92 is configured to retainably engage a blade extender 94. In this regard, the blade 92 and extender 94 are configured to include a dovetail joint 96a, 96b therebetween. Use of the extender 94 allows for adjustment of the length and/or profile of the blade without comprising the integrity of the structure, since the blade 92 remains permanently and rigidly affixed to its respective arm 12. This represents a significant improvement over prior art retractor structures which include removable blades. In such retractors, the removable blades are affixed to the arm by clamps, screws or other such releasable joining mechanisms; and it has been found that the presence of these mechanisms, in addition to compromising the integrity of the retractor, interferes with the surgeon's vision and access to the surgical site, since such structures present a bulky impediment at the surface of the skin. In contrast, the retractor of FIG. 7 is strong and stable, since the blade 92 is permanently affixed to the arm 12 at a point where significant stresses occur. Furthermore, the extension portion 94 joins the blade 92 at a location well within the surgical channel. In a typical implementation of this embodiment, the joint 96 between the blade 92 and extension portion 94 is typically made at a point two or more centimeters from the junction point between the blade 92 and arm 12. In this manner, a strong, secure joint is achieved, and the surgeon's view of, and access to, the surgical field is not impeded. As shown in FIG. 7A, the extension portion 94 is joined to the blade 92 by a dovetail joint; however, it is to be understood that these members may be otherwise joined as will be apparent to one of skill in the art. In some specific embodiments, mechanisms for effecting the junction may be conveniently disposed on the tissue contacting side of the retractor blade 92 so that such connector structures are not disposed in the surgical channel.

Yet other embodiments of extender blade may be implemented in accord with the present invention, and FIG. 7B depicts one such alternative embodiment. The FIG. 7B retractor 100 includes a blade 102, a portion of which is shown in phantom outline. The blade 102 includes a locking mechanism comprised of a locking pin 104 having a first 106a and second 106b notch defined therein. The pin 104 engages a biasing spring 108. A portion of the pin 104 projects from the remainder of the blade 102, and the remainder of the pin 104 is captive in the blade 102.

The FIG. 7B embodiment includes an extender 110, which has a first and second notched pin 112a, 112b projecting therefrom. In use, the pins 112 are passed into the blade 102 through appropriately configured holes 114a, 114b; the projecting portion of the pin 104 is depressed so as to move the notches 106a, 106b into alignment with the holes 114a, 114b so as to permit the pins to pass fully into the blade 102. When the pin is released, the spring 108 biases the pin 104 back to its initial location thereby locking the extension portion 110 onto the blade 102.

In accord with the present invention, retractors such as the aforedescribed embodiments are employed to create the keyhole access passage to the surgical site. In that regard, an opening which is most preferably no more than 20 millimeters in any maximum dimension is formed through a patient's skin. This opening is separated from the ultimate surgical operating field by intervening tissue. Following the formation of the incision, the intervening tissue is displaced, most preferably through the use of a retractor of the type described hereinabove. In this regard, most preferably, a passage is first formed through the intervening tissue by the use of a dilator. Appropriate dilators are known in the art, and one type of dilator comprises a series of mandrels configured as elongated cylindrical members. The mandrels are of progressively larger diameter, and they are inserted serially into the tissue. The mandrels push apart the fibers of the tissue with minimal tearing or breakage. The final mandrel may also include a cylindrical sleeve member or cannula disposed about its outside circumference. After this final dilator is inserted into the tissue, the central mandrel is withdrawn, leaving the cannula in place. This cannula retains the tissue in its dilated state and allows for insertion of the retractor, after which the cannula is withdrawn and the retractor is expanded to create a yet wider passage through the tissue. The retractor may be inserted into the central bore of the cannula, or it may be slid along the outside of the cannula. In other instances, the cannula may have a "C" shaped cross section which will facilitate placement and use of the retractor. In some instances, a retractor of the type shown in FIG. 6 may function dually as a cannula and as a retractor, in which instance the retractor of FIG. 6 is first clamped about the final dilator mandrel and inserted into the tissue therewith, following which it is expanded to displace tissue and the mandrel withdrawn.

Other configurations of tissue dilator are known in the art. For example, some dilators comprise an expansible cannula in which the diameter thereof may be increased after insertion into the tissue. Yet other types of dilator are known in the art, and all of such dilators may be employed in the practice of the present invention. Also, while the invention has been described as being practiced in connection with the use of a cannula, in some instances the cannula may be dispensed with.

Figure 8:
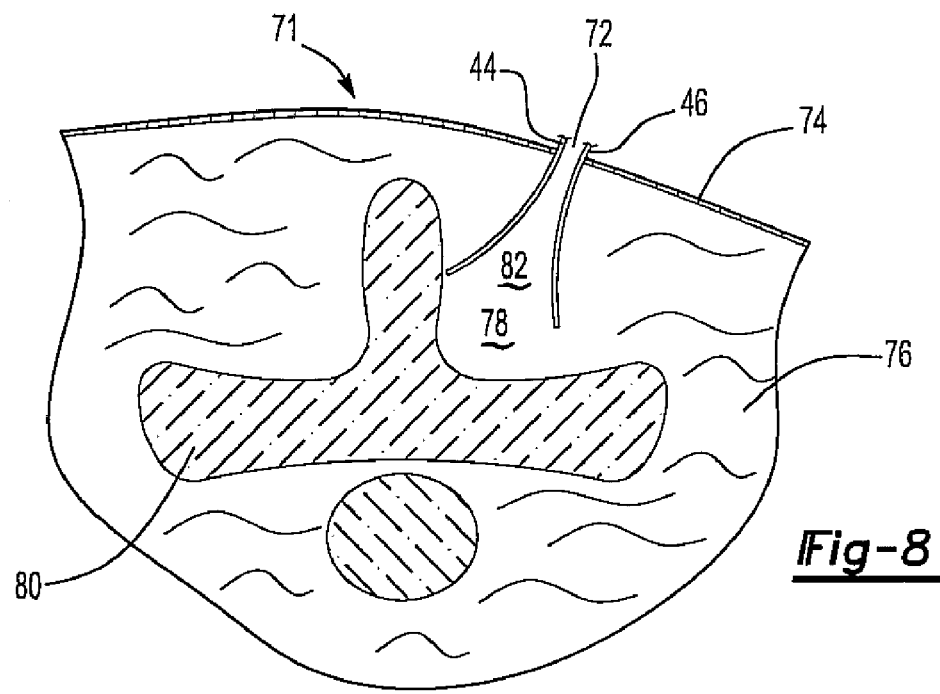
FIG. 8 is a cross-sectional view of the retractor of the present invention as utilized in a surgical procedure.

Referring now to FIG. 8, there is shown a cross-sectional view of a portion of a patient's body 71 illustrating the surgical method of the present invention. As will be seen from FIG. 8, a relatively small opening 72 is formed through a patient's skin 74. Most preferably, this opening will not be larger than 20 millimeters in its greatest dimension. A pair of retractor blades 44, 46 displace tissue 76 so as to provide access to a surgical field 78 in which a portion of a patient's spine 80 is exposed. As will be seen from FIG. 8, the passage 82 through the tissue 76 is flared so that it widens as it progresses from the skin 74 to the surgical field 78. In this manner, the cross-sectional area of the surgical field 78 is greater than the cross-sectional area of the opening 72 in the patient's skin 74. This keyhole passage provides maximum visualization of the surgical field 78 while minimizing the incision through the patient's skin 74. The keyhole passage allows for direct visualization of the surgical field 78 and maximizes the space available for surgery. The use of the retractor minimizes tissue trauma, and the relatively small size of the opening in the skin 74 minimizes scarring and facilitates closure of the surgical wound.

It is to be understood that while the present method and apparatus have been described with particular reference to spinal surgery, the principles of the present invention may be readily adapted to other surgical procedures which are not limited to the spine or to the formation of a keyhole channel. As will be apparent, the retractor and method of the present invention may also be utilized in veterinary procedures, as well as in non-medical applications. Also, while specific embodiments of retractor have been described, it is to be understood that yet other modifications and configurations thereof may be implemented in accord with the teaching herein. The foregoing drawings, discussion and description are meant to be illustrative of specific embodiments of the invention, but they are not meant to be limitations upon the practice thereof. It is the following claims, including all equivalents, which define the scope of the invention.

The invention claimed is:

1. A method for performing a spinal surgery, said method comprising the steps of:
    forming an opening through the skin of a patient, said opening having a maximum dimension of no more than 20 millimeters, said opening being separated from a surgical field by intervening tissue;
    displacing said intervening tissue between said opening and said surgical field so as to form a keyhole channel therethrough, said keyhole channel being characterized in that it increases in width as it progresses from said opening to said surgical field; whereby the cross-sectional area of said surgical field exposed by said channel is greater than the cross-sectional area of said opening; and
    performing a surgical procedure at said surgical field.

2. The method of claim 1, wherein the step of performing a surgical procedure comprises performing said surgical procedure under direct visualization.

3. The method of claim 1, wherein the step of displacing said tissue comprises:
    providing a surgical retractor having a pair of separable, tissue engaging blades;
    providing a passage through said intervening tissue;
    inserting the blades of said retractor into said passage; and
    separating the blades of said retractor whereby said retractor displaces said intervening tissue so as to form said keyhole channel.

4. The method of claim 3, wherein said retractor comprises a first and a second arm, each arm including a first end which defines a handle portion, and a second end having one of said retractor blades projecting therefrom, said arms being pivotally connected together at a connection point between their respective first and second ends; wherein the retractor blade of the first arm and the retractor blade of the second arm each include a junction end at which said blade is permanently affixed to its respective arm, and a free end; and wherein, said arms and blades are configured and disposed so that when, in the use of the retractor, the arms are pivoted about said connection point, the free ends of the blades are always at least as far apart as said junction ends.

5. The method of claim 4, wherein said retainer is configured so that when the arms are pivoted about the connection point, the free ends of the blades are always farther apart than are said junction ends.

6. The method of claim 4, wherein said retractor is configured so that the blades thereof each have a width dimension measured transverse to a longitudinal axis thereof, which longitudinal axis extends from the free end thereof to the junction thereof, said width dimension being no greater than 20 millimeters.

7. The method of claim 6, wherein said width dimension is no greater than 15 millimeters.

8. The method of claim 1, wherein the step of forming said channel comprises inserting a dilator into said intervening tissue, said dilator being operable to form said passage.

9. The method of claim 8, wherein said dilator comprises a series of dilator mandrels, each having a different diameter.

10. The method of claim 8, wherein said dilator comprises an expansible member.

11. The method of claim 8, wherein said dilator comprises a cylindrical member having a C-shaped cross section.

12. The method of claim 8, wherein the blades of a surgical retractor are inserted into said channel before said dilator is withdrawn therefrom.

13. The method of claim 1, wherein said procedure is a discectomy.

14. The method of claim 1, wherein said procedure is a laminectomy or discectomy carried out via microsurgical techniques.

* * * * *